United States Patent
Dervieux

Patent Number: 6,026,327
Date of Patent: Feb. 15, 2000

[54] HAND HELD ELECTRICAL STIMULATOR FOR PAIN RELIEF USING CYLINDRICAL ELECTRODE HEAD

[76] Inventor: Dominique Dervieux, Le Panoramer, 31, corniche André-de-Joly, F-06300 Nice Cédex, France

[21] Appl. No.: 09/029,344
[22] PCT Filed: Aug. 30, 1996
[86] PCT No.: PCT/FR96/01338
§ 371 Date: Feb. 27, 1998
§ 102(e) Date: Feb. 27, 1998
[87] PCT Pub. No.: WO97/07855
PCT Pub. Date: Mar. 6, 1997

[30] Foreign Application Priority Data

Aug. 31, 1995 [FR] France ................................. 95 10406

[51] Int. Cl.⁷ .................. A61N 1/32; A61N 1/18
[52] U.S. Cl. .................. 607/46; 607/50; 607/145; 607/150
[58] Field of Search ............... 607/46, 50, 74, 607/145, 149, 150

[56] References Cited

U.S. PATENT DOCUMENTS

| | | |
|---|---|---|
| 1,532,463 | 4/1925 | Winterfield ........................... 607/150 |
| 4,033,356 | 7/1977 | Hara ...................................... 607/74 |
| 4,175,551 | 11/1979 | D'Haenens et al. ................. 601/20 |
| 4,920,981 | 5/1990 | Dervieux .............................. 607/145 |
| 5,203,349 | 4/1993 | Kogan .................................. 607/145 |
| 5,514,167 | 5/1996 | Smith et al. .......................... 607/75 |

FOREIGN PATENT DOCUMENTS

| | | | |
|---|---|---|---|
| 0 603 451 A1 | 6/1994 | European Pat. Off. | ......... A61N 1/26 |
| 1137482 | 5/1957 | France . | |
| 2 621 827 | 4/1989 | France | ......... A61N 1/32 |
| 2 624 748 | 6/1989 | France | ......... A61N 1/26 |

Primary Examiner—William E. Kamm
Assistant Examiner—Carl H. Layno
Attorney, Agent, or Firm—Lydon & Brown, LLP

[57] ABSTRACT

Portable device for relief of pain and contractures and skin rejuvenation comprising a head (10) for applying electric current pulses to the skin of a user and a handle (16) held by the user's hand. The head has the shape of a cylinder portion of which the directrix has a convex shape, the head having at least one electrode (22, 24) situated on its external surface or at a constant distance from said external surface and of which at least one portion is situated on each generatrix of the cylinder part susceptible to be in contact with the user's skin. Thus, the head is always in contact with the user's skin by one of the generatrices lines of the cylinder portion comprising an electrode portion independently of the inclination of the head with respect to the user's skin.

13 Claims, 4 Drawing Sheets

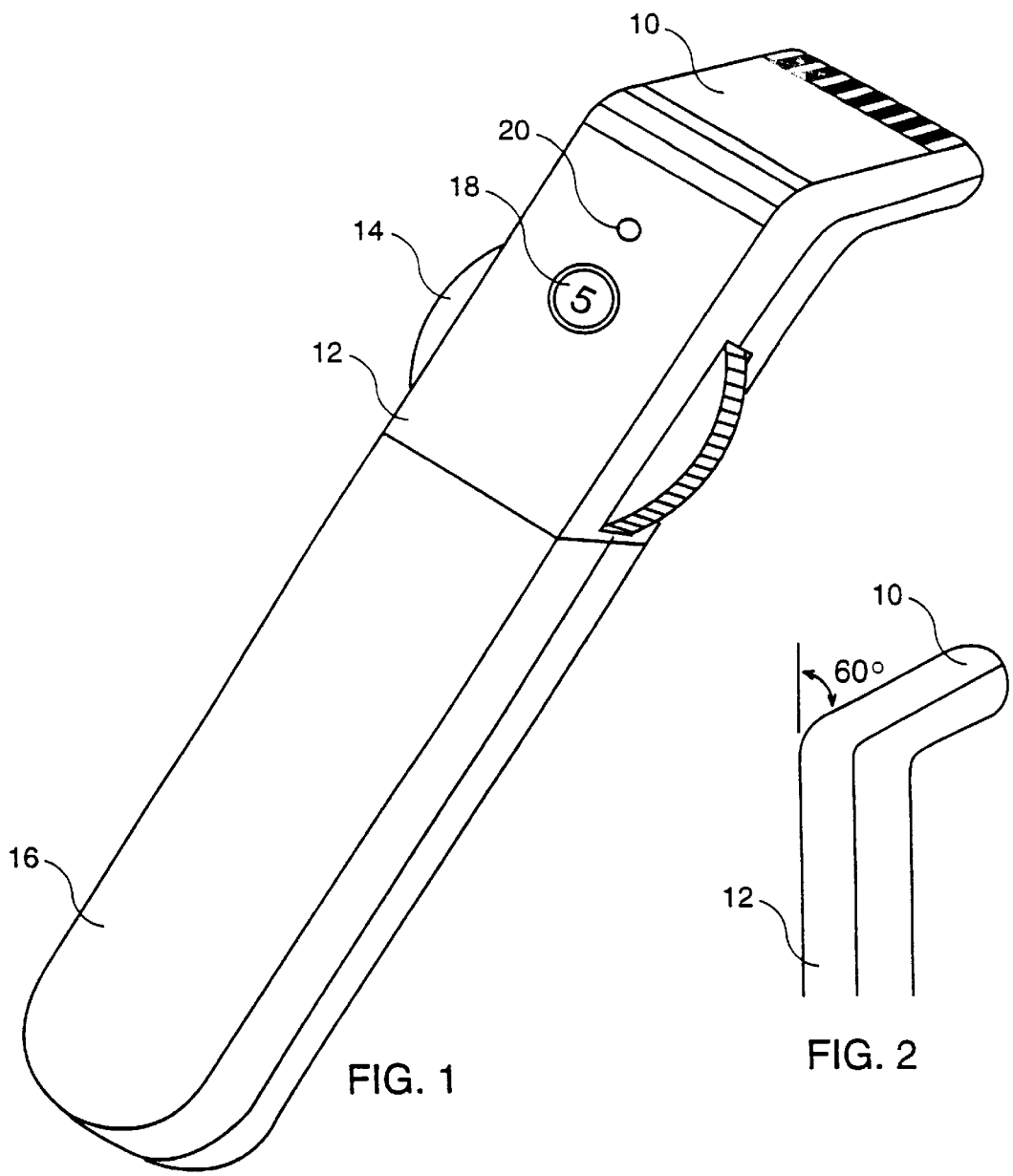
FIG. 1
FIG. 2
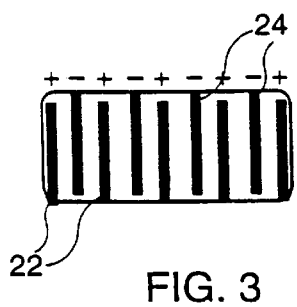
FIG. 3
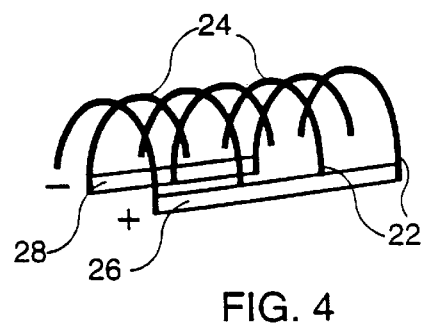
FIG. 4

HAND HELD ELECTRICAL STIMULATOR FOR PAIN RELIEF USING CYLINDRICAL ELECTRODE HEAD

TECHNICAL FIELD

The present invention relates generally to devices providing pain relief by means of electric pulses applied to the user's skin, and particularly to a high efficiency device of this type providing no discomfort to the user, whatever the position of the device against the skin.

PRIOR ART

We already know pain relief devices based on the application of electric pulses wherein the electric current is produced by a piezoelectric discharge. The patent application EP-0214136 issued to Dervieux on Mar. 18, 1987, describes a pain relief device based on piezoelectric sparks. The application head is made up of a double-pole electrode wherein either one pole is in direct contact with the skin and the other one is located at a distance from the skin, or both poles are located at a distance from the skin. When the piezoelectric crystal is compressed, a discharge of static electricity warm electrons occurs and hit the skin, with salutary effects.

According to another type of device, the electric discharges are not produced through piezoelectric components, but through a "relaxing" type generator. The patent application FR-2624748 issued to Kogan on Jun. 23, 1989 describes such a type of device wherein electric discharges applied on the user's skin are produced by a "R.C." type generator.

Other devices of the same type, also based on electric pulses applied to the user's skin, are described in patents FR-A-2.621.827, ES-A-0.603.451 and EP-A-0.387.176.

All these devices comprise a head that must be kept in contact with the skin for applying electric pulses. Since the skin's surface is not flat, it is very difficult for the user to permanently keep the head in contact with the skin. The slightest tilting of the head increases the distance between the electrodes and the skin, increases the pulse voltage and intensity, especially on wet skin or into damp air. This way, one-tenth millimeter gap produces a 100 volts voltage increase, and one millimeter gap leads to a 1000 volts increase. This voltage is doubled if both poles of the double-pole electrode are set back from the application head. Finally, untimely discharges occur on these devices, particularly when approaching or removing the device.

The electrodes used in all these devices generally have a complex application surface with many pits capable of retaining various dirty elements that might be detrimental to hygiene or cause infections. Furthermore, such surfaces are not suited for sticking renewable hygienic protective covers.

Finally, for using the device on wet skins, one electrode must be in contact with the skin while the other one must not touch the latter, at the risk of cancelling its efficiency, and be kept at a distance of about one millimeter from it (that corresponds to a 1000 volts voltage). Thus, the lower limit of the operating voltage is high for this kind of device.

All this contributes to a painful and unpredictable use of these devices, due particularly to the intensity increase when their flat head is tilted against the skin surface, the occurrence of untimely discharges, the bad distribution of discharges that decreases the efficiency, leading to fear and most often reject reactions from the user.

DISCLOSURE OF THE INVENTION

This is why the object of the invention is to provide a pain relief device through electric pulses that has none of the above drawbacks whatever its operating position.

Another object of the invention is to provide a pain relief device through constant voltage electric pulses, whatever the skin is dry or wet and whatever the tilting angle of the application head against the skin.

The invention relates therefore to a portable device for relieving pain and contractures, and for skin rejuvenation comprising a handle held by the user's hand and a head for applying electric pulses to the skin of the user, having the shape of a cylinder portion whose directrix has a convex shape. The head for applying electric pulses comprises at least one electrode for generating the pulses, located on the outer surface of the cylinder or at a constant distance from this outer surface, and a portion of which, at least, is located on each generatrix likely to be in contact with the user's skin, the head being always in contact with the user's skin through one generatrix of the cylinder portion comprising the electrode portion, whatever the tilting angle of the head against the user's skin surface.

According to a first characteristic of the invention, the head for applying electric pulses comprises a first set of electrodes having a given polarity at a given time and a second set of electrodes whose polarity is the opposite of the one of the first set at the same given time, all electrodes being parallel each other and perpendicular to the generatrices of the head having the shape of a cylinder portion, and the electrodes of both sets being located alternately.

According to a second characteristic of the invention, the head for applying electric pulses is covered with a layer of insulating material such as a constant thickness porous non-woven fabric plaster, so that the electrodes are spaced out from the skin by a constant distance, for example lower than 1 mm, whatever the tilting angle of the head against the skin.

The configuration of the device according to the invention makes possible its use on the whole skin regions of the user in spite of applying angles that may vary up to 180° against the skin surface, with neither intensity variations nor untimely discharge.

Such a device has many advantages, and particularly enables on the one hand to use minimum voltages, much lower than the voltages of previous devices that used several thousands of volts while this device does not require more than several hundred volts, and on the other hand to limit and electronically regulate the maximum intensity of the discharges at a level lower than the one that produces pain, thus doing away with untimely discharges.

BRIEF DESCRIPTION OF THE DRAWINGS

The objects, features and other characteristics of the invention will become more apparent from the following description with reference to the accompanying drawings, in which:

FIG. 1 shows a perspective view of a preferred embodiment of the device according to the invention, FIG. 2 shows a cross-section of the applying head tilted by an angle of 60° against the handle axis, FIG. 3 shows the front view of an applying head comprising parallel electrodes with alternate polarities, perpendicular to the cylinder portion, FIG. 4 shows diagrammatically a perspective view of the head whose front face is shown on FIG. 3.

DETAILED DESCRIPTION OF THE INVENTION

Figure 5:
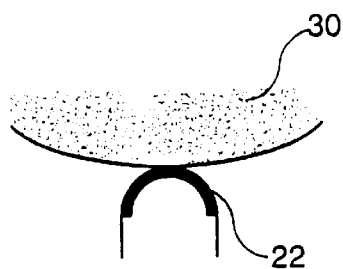
FIG. 5 shows a cross-section of the applying head according to the invention in contact with the user's skin.

A first embodiment of the device according to the invention shown on FIG. 1 is made up of a head 10 for applying electric pulses on the user's skin, a body 12 having an elongated and flattened shape, comprising a switch 14 for switching on and of the device and a handle 16 held by the user. In the body 12, a window 18 displays a number indicating the voltage level of the device, for example 0, 1, 2, 3, 4, 5, and a led 20 indicates that the device is on.

As it can be seen on the FIG. 2, the head 10 is tilted against the body 12 by an angle of about 60° to make easier the orientation of the device on the skin when it is held by the user. The shape of the head 10 is a cylinder portion whose directrix is preferably circular but may have any other convex shape.

In a preferred embodiment, the head comprises electrodes with alternate polarities, for example positive electrodes 22 (at a given time) alternate with negative electrodes 24 (at the same time), as shown on FIG. 3. The electrodes 22 and 24 are parallel each other, perpendicular to the generatrices of the cylindrical head and spaced apart by a distance of about 1 to 3 mm.

The electrodes are arranged as shown in perspective on FIG. 4, all positive electrodes 22 at a given time being connected to the positive terminal 26, thus forming a comb, and all negative electrodes 24 at the same time being connected to the negative bar 28, forming also a comb.

FIG. 5 illustrates a cross-section of the head, the electrodes 22 (or 24) being in contact with the user's skin 30. This arrangement of electrodes according to an arc of a circle and the application of the cylindrical head through a generatrix ensure a permanent contact of the electrodes on the skin even if the head forms a high tilting angle against the perpendicular to the skin, said angle being likely to reach 90° on both sides.

Figure 6:
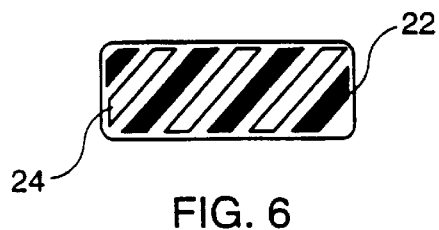
FIG. 6 shows the front face of an applying head comprising parallel electrodes slanted against the generatrices of the cylinder portion.

Although the arrangement shown on FIG. 3 is the preferred one, it is possible to arrange the electrodes so that they are slanted against the generatrices of the cylindrical head, as shown on FIG. 6. As in the previous case, a part of positive or negative electrodes is always in contact with the skin, whatever the tilting angle of the head against the skin.

Figure 7:
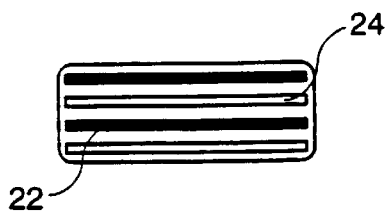
FIG. 7 shows the front face of an applying head comprising electrodes parallel to the generatrices of the cylinder portion.

Actually, applying the head on the skin, even with a low pressure, produces a slight depression in the skin and thus a contact of the head with the skin through a stripe having a certain width, for example 3 to 4 mm. It is thus possible to arrange the electrodes in the manner shown on FIG. 7, namely parallel to the generatrices of the cylinder since the gap between negative and positive electrodes is always narrower by 1 to 3 mm than said contact strip of the head with the skin.

Figure 8:
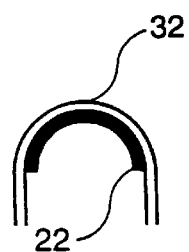
FIG. 8 shows the cross-section of an applying head whose electrodes are covered with a layer of an insulating material.

In a variant of the previous embodiment, the electrodes 22 and 24 can be covered with a layer 32 of an insulating material having a constant thickness as illustrated on FIG. 8. Such a material that ensures hygiene and protection can for example be porous non-woven fabric plaster. The thickness of the protective layer must not exceed 1 mm in order to avoid the supply of high voltages.

Figure 9:
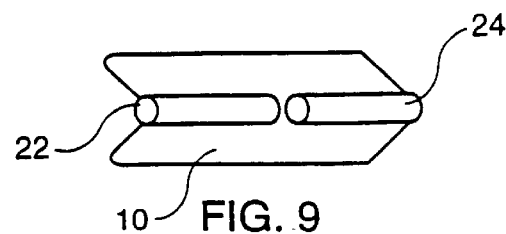
FIG. 9 shows the cross-section of an applying head whose electrodes are made of two cylindrical bars lined up with each other.

Another embodiment consists in using an applying head exclusively made up of two electrodes having the shape of a cylinder. As shown on FIG. 9, the electrodes 22 and 24 have the shape of circular cross section bars located at the end of the applying head 10 lined up each other and spaced apart by a gap included between a few tenths of mm and 5 mm. It is to be noted that the round shape of the electrodes enables the tilting of the head on both sides while keeping the electrodes in contact with the skin.

Figure 10:
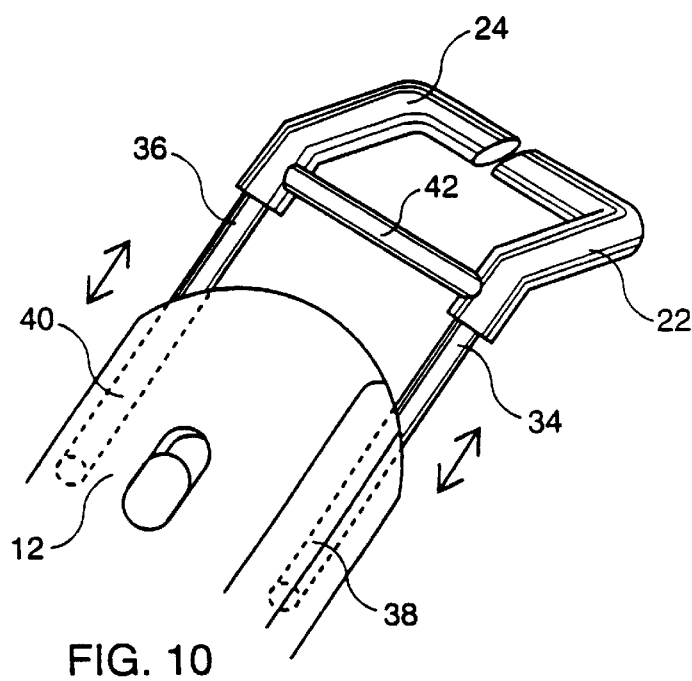
FIG. 10 shows diagrammatically an embodiment of the invention wherein the applying head is made up of two electrodes that form arms lined up with each other.

This embodiment can also be produced in the form of the device diagrammatically shown on FIG. 10. The two electrodes 22 and 24 are two arms fixed on the device by means of two rods 34 and 36 that can possibly be telescopic, thanks to slides 38 and 40 located in the body 12 of the device. In such a case, the length of both rods 34 and 36 can be adjusted in the direction of the arrows according to the wishes of the user. The two rods 34 and 36 are kept together with a constant gap thanks to the connecting part 42.

Figure 11:
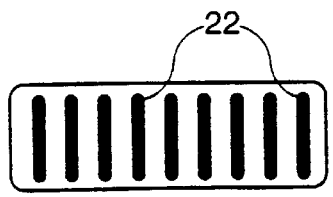
FIG. 11 shows the front face of an applying head comprising parallel electrodes having the same polarity.

In a third embodiment, only one electrode (for example the electrode 22, positive at a given time) is placed on the applying head, the other electrode (negative at the same time) being located in the body of the device in permanent contact with the user's hand. In such a case, the electrode 22 can have the form of conductive bars all connected to the device positive bar, as shown on FIG. 11.

Figure 12:
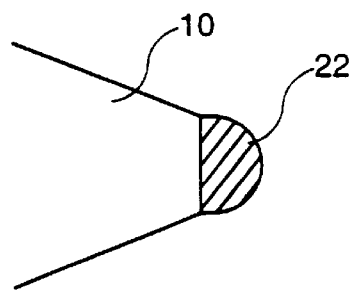
FIG. 12 shows a cross-section of an embodiment wherein the applying head is made up of a single cylindrical electrode.

The electrode can also have the form of a semicircular bar placed at the end of the head 10, as shown on FIG. 12.

Figure 13:
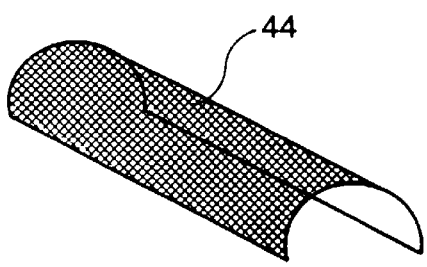
FIG. 13 shows a grid that makes up a single polarity electrode, as a variation of the previous embodiment.
Figure 14:
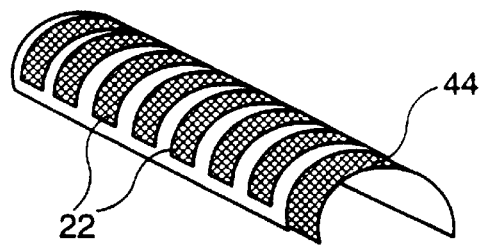
FIG. 14 shows the assembly that makes up an applying head comprising the grid shown on FIG. 13 covered with a layer of an insulating material provided with parallel slots that form the electrodes.
Figure 15:
FIGS. 15, 16, 17 and 18 show several shapes of slots that make up the electrodes insulating material layer used in the embodiment of the FIG. 14.
Figure 16:
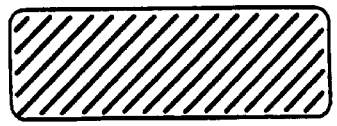
Figure 17:
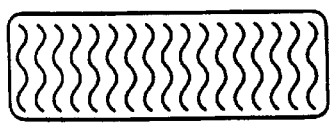
Figure 18:
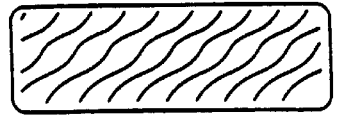

However, this third embodiment is preferably produced in the form of a grid 44 that plays the role of the electrode 22 shown on FIG. 13. This grid is covered with a layer 46 of an insulating material with a constant thickness ranging from 1/10 mm to 2 mm comprising slots that make up as so many electrodes 22 of the same polarity (for example positive) as shown diagrammatically on FIG. 14. These slots can have various shapes shown on FIGS. 15, 16, 17 and 18 and have a variable width. Whatever the shape, the number or the width of slots that play the role of electrodes, it is clear that, due to the shape of the head as shown on FIG. 14, a portion of each said electrode will always be situated at a constant distance from the user's skin through the layer 44, whatever the tilting angle of the head against the skin surface.

Whether the electrodes are in direct contact with the skin or are spaced out from it by a hygienic protective insulating material with constant thickness or even a piece of clothing, the fundamental principle of the device described above is applying on the skin electric pulses having a fixed frequency ranging from 10 to 150 Hz and a constant voltage lower than 2000 volts.

In order to be efficient, these pulses must produce tingling feelings with a maximum intensity (variable, depending on individuals) that must not, however, reach the pain threshold. The physiologic active mechanism of this type of device is described in the French patent 84 07087.

The generation of electric pulses can be performed in two ways. In a first mode, we get a manually controlled piezoelectric type generator. It may comprise a spark gap or discharge capacitor made up of a continuity break in the insulating material of the high voltage electric wire that goes to the head of the device, obtained by stripping the metallic wire at a distance ranging from 1/10 mm to a few millimeters from the generating metallic stirrup that makes up the other pole.

Figure 19:
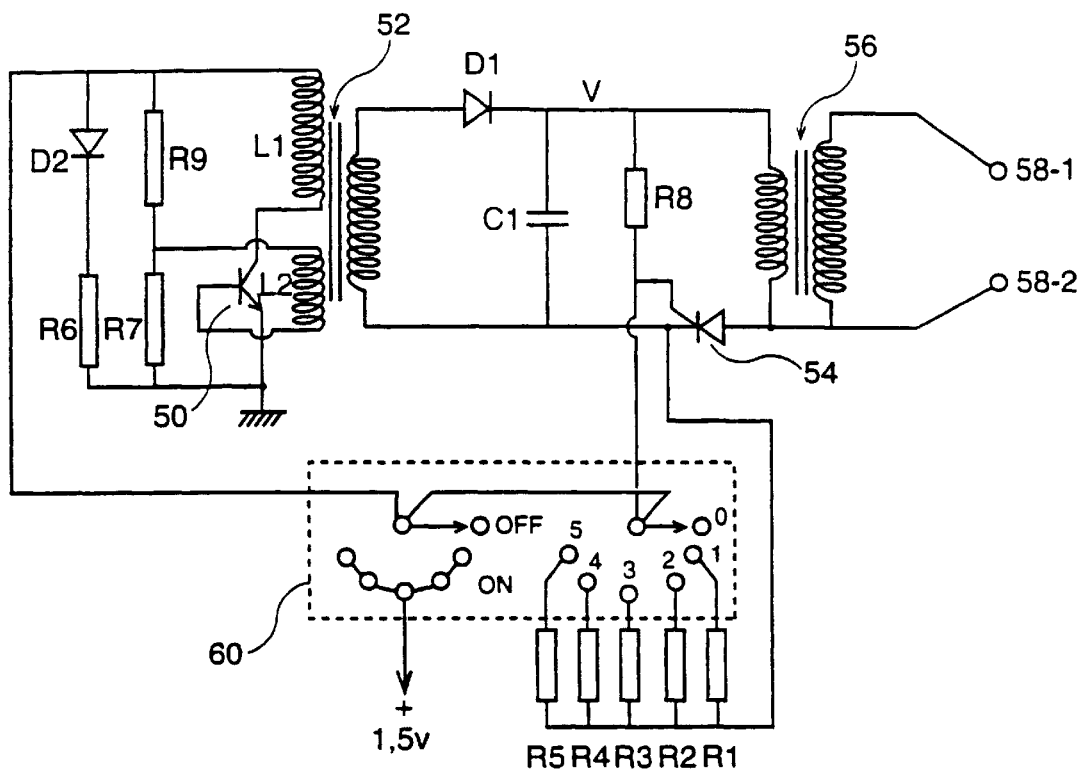
FIG. 19 is the diagram of a preferred embodiment of the electronic circuit.

Generating the pulses can also be performed through an electronic circuit as shown on FIG. 19. In such a circuit, the transistor 50 is used as a switch that connects alternately an inductance L1 forming a first primary winding of a transformer 52 to a 1.5 volt voltage source that can be a battery housed in the handle of the device. The transformer 52 delivers an induced reaction voltage in the inductance L2 that forms a second primary winding applied to the base of the transistor 50. Since the diode D1 of the secondary winding is reverse biased, the secondary winding of the transformer 52 is an open circuit, and consequently, the intensity change in L1 is practically linear during the conduction period of the transistor 50. During this period, the collecting current intensity of the transistor 50 increases up to its maximum value, imposed by the base current corresponding to an induction value lower than the saturation. At this time, the variation of the collecting current decreases (namely the derivative di/dt tends to zero) and the induced voltage in the winding L2 decreases while the equivalent resistance of the transistor 50 becomes very high. As the effect is cumulative, there is practically a sudden break of the collector intensity in the primary winding. It is to be noted that the resistors R6, R7, R9 as well as the diode D2 are typical elements for this type of circuit, and their role is to set flowing paths for the current.

The direction reversal of the current in the primary winding of the transformer 50 produces the direction reversal of the voltage at the secondary winding terminals. The diode D1 becomes conductive. The electromagnetic energy ½ L.I2 stored during the first part of the cycle is transferred to the secondary winding and charges the capacitor C1. Thus, the circuit has played the role of a DC/AC converter.

In the second part of the circuit shown on FIG. 19, the trigger-gate of a thyristor 54 is connected to the terminal of a resistor R8 that is a part of a dividing bridge, what changes the voltage to be reached at the capacitor C1 for triggering the thyristor 54. When this voltage V is reached, the thyristor 54 becomes conductive and the capacitor C1 discharges into the primary winding of a high voltage transformer 56, what produces a pulse in the secondary winding whose voltage value depends on the transformer's voltage ratio, and supplied between the output terminals 58-1 and 58-2 connected to the electrodes of the device.

The switch 60 provided with five positions plus the disconnected position 0, enables to connect the 1.5 volt voltage through resistors R1, R2, R3, R4, and R5 having increasing values. The value of the connected resistor defines the voltage level V reached within a period whose duration depends on this value, and thus produces the frequency variation of the pulses supplied between the terminals 28, as well as the voltage variation. It is to be noted that, the more the output voltage increases (when going from R1 to R5), the more the pulse frequency decreases and vice versa.

Although the output voltage of the device can take only five values in the above embodiment, it is possible to provide for a greater number of resistors, and thus a greater number of values. But it is also possible to replace the discrete resistors with a rheostat enabling to change the output voltage continuously.

I claim:

1. Portable device for relief of pain and contractures and for skin rejuvenation comprising a head for applying electric pulses to the skin of a user and a handle held by the user's hand, wherein said head has the shape of a cylinder portion whose directrix has a convex shape and comprises at least one electrode for generating the electric pulses, located on the outer surface of said cylinder or at a constant distance from this outer surface, and a portion of which, at least, is located on each generatrix of said cylinder likely to be in contact with the user's skin, said head being always in contact with the user's skin through one of the generatrices of said cylinder portion comprising said electrode portion, whatever the tilting angle of the head against the users's skin surface, wherein said head for applying electric pulses comprises electrodes having opposite polarities at a given time, said pulses being produced between two electrodes having opposite polarities through the user's skin, wherein said head for applying electric pulses comprises a first set of electrodes having a given polarity at a given time and a second set of electrodes having a polarity opposite to the one of the first set at said given time, the electrodes of the given second set being arranged alternately with the electrodes of the first set, and wherein electrodes from said sets are parallel each other and perpendicular to the generatrices of said head having the shape of a cylinder portion.

2. Device according to claim 1, wherein said first set of electrodes forms a comb connected to a terminal having a given polarity at a given time, and said second set of electrodes forms a comb connected to a terminal having an opposite polarity at the same time.

3. Device according to claim 1, wherein electrodes from said sets are parallel each other and to the generatrices of said head having the shape of a cylinder portion, two adjacent electrodes having opposite polarities at a given time being spaced apart by a distance lower by 1 mm to 3 mm to the width of skin strip in contact with a generatrix of said cylinder portion so that at least two electrodes having opposite polarities be always in contact with the skin or located at a constant distance from the skin whatever the tilting angle of said head against the user's skin surface.

4. Device according to claim 1, wherein said head comprises two electrodes having opposite polarities and having the shape of circular cross-section rods, both electrodes being placed along a generatrix of said head having the shape of a cylinder portion and being spaced apart by a distance ranging from a few tenths of mm to 5 mm.

5. Device according to claim 1, wherein said head is itself made up of two electrodes having opposite polarities at a given time and having the shape of two circular cross-section cylindrical arms lined up each other and spaced apart by a distance ranging from a few tenths of mm to 5 mm.

6. Device according to claim 5, wherein said head is fixed to the remaining device through telescopic rods.

7. Device according to claim 1, wherein said head is covered with a layer of insulating material, so that said electrodes are spaced out from the user's skin by a constant distance, whatever the tilting angle of the head against the skin.

8. Device according to claim 7, wherein said constant distance is less than 1 mm.

9. Device according to claim 7, wherein said insulating material comprises non-woven fabric plaster.

10. Device according to claim 1, wherein said handle is linked to said head for applying electric pulses by means of a body lined up with said handle, said head forming an angle ranging from 45° to 90° with the axis of said body.

11. Device according to claim 1 wherein a circuit for generating electric pulses further comprises a direct current source, a DC/AC voltage converter comprising a transistor alternately conductive and blocked and a transformer providing alternative voltage pulses, and a high voltage transformer whose frequency and voltage at the output terminals depend on the triggering of a thyristor according to the power level imposed by a switch actuated by the user, the output voltage increasing when the frequency decreases, and vice versa.

12. Device according to claim 1, wherein said head for applying electric pulses comprises a set of at least one electrode having a given polarity at a given time, the other electrode having an opposite polarity at said time being located on said handle in contact with the user's hand.

13. Device according to claim 12, wherein said head is made up of a grid having said given polarity at a given time, covered with an insulating material layer with constant thickness comprising parallel slots having any shape thus making up said set of electrodes of said given polarity.

* * * * *